(12) United States Patent
Cai (10) Patent No.: US 10,258,315 B2
(45) Date of Patent: *Apr. 16, 2019

(54) SYSTEMS AND METHODS FOR REDUCING NON-UNIFORM ROTATION DISTORTION IN ULTRASOUND IMAGES

(71) Applicant: Boston Scientific SciMed, Inc., Maple Grove, MN (US)

(72) Inventor: Anming He Cai, San Jose, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1099 days.

This patent is subject to a terminal disclaimer.

(21) Appl. No.: 14/622,333

(22) Filed: Feb. 13, 2015

(65) Prior Publication Data

US 2015/0150540 A1 Jun. 4, 2015

Related U.S. Application Data

(63) Continuation of application No. 13/239,160, filed on Sep. 21, 2011, now Pat. No. 8,956,299.
(Continued)

(51) Int. Cl.
*A61B 8/08* (2006.01)
*A61B 8/12* (2006.01)
*A61B 8/00* (2006.01)

(52) U.S. Cl.
CPC .............. *A61B 8/5269* (2013.01); *A61B 8/12* (2013.01); *A61B 8/4461* (2013.01); *A61B 8/5207* (2013.01); *A61B 8/445* (2013.01)

(58) Field of Classification Search
None
See application file for complete search history.

(56) References Cited

U.S. PATENT DOCUMENTS 5,699,806 A 12/1997 Webb et al.
6,019,726 A 2/2000 Webb
(Continued)

OTHER PUBLICATIONS

International Search Report and Written Opinion for International Patent Application No. PCT/US2011/052644 dated Dec. 29, 2011.
(Continued)

*Primary Examiner* — Katherine L Fernandez
*Assistant Examiner* — Michael S Kellogg
(74) *Attorney, Agent, or Firm* — Lowe Graham Jones PLLC; Bruce E. Black (57) ABSTRACT

A method for generating an ultrasound image includes receiving an image frame comprising consecutive ultrasound scan lines obtained using a rotating ultrasound imaging arrangement and determining at least a first cross-correlation value and a second cross-correlation value for each of a plurality of the scan lines. For each individual scan line of the plurality of scan lines, the first cross-correlation value comprises a cross-correlation coefficient between a first subframe comprising a plurality of consecutive scan lines including the individual scan line and a second subframe comprising a plurality of scan lines shifted from the first subframe by a first integer value. The second correlation value comprising a cross-correlation coefficient between the first subframe and a third subframe comprising a plurality scan lines shifted from the first subframe by a second integer value that is different from the first integer value. The method further includes evaluating, individually for multiple scan lines of the plurality of scan lines, whether the scan line being evaluated exhibits non-uniform rotation distortion using at least one of the first and second correlation values for the scan line being evaluated. A correction for non-uniform rotation distortion is applied using at least one of the first and second correlation values for at least one of the plurality of scan lines. An ultrasound image is generated
(Continued)

using at least the plurality of scan lines with the applied correction and the ultrasound image is displayed.

20 Claims, 5 Drawing Sheets

Related U.S. Application Data (60) Provisional application No. 61/407,854, filed on Oct. 28, 2010.

(56) References Cited

U.S. PATENT DOCUMENTS

| | | | |
|---|---|---|---|
| 6,152,878 | A | 11/2000 | Nachtomy et al. |
| 6,267,727 | B1 * | 7/2001 | Teo .................... A61B 8/12 600/468 |
| 6,945,938 | B2 | 9/2005 | Grunwald |
| 7,024,725 | B2 | 4/2006 | Homberg |
| 7,246,959 | B2 | 7/2007 | Nakatani |
| 7,306,561 | B2 | 12/2007 | Sathyanarayana |
| 2006/0100522 | A1 | 5/2006 | Yuan et al. |
| 2006/0106320 | A1 | 5/2006 | Barbato |
| 2006/0173350 | A1 | 8/2006 | Yuan et al. |
| 2006/0253028 | A1 | 11/2006 | Lam et al. |
| 2007/0016054 | A1 | 1/2007 | Cao et al. |
| 2007/0038111 | A1 | 2/2007 | Rehrig et al. |
| 2007/0106155 | A1 * | 5/2007 | Goodnow ................ A61B 8/12 600/437 |

OTHER PUBLICATIONS

Adjacent | Define Adjacent at Dictionary.com, accessed Oct. 4, 2013, by Dictionary.com.

Azimuthal Registration of Image Sequences Affected by Nonuniform Rotation Distortion by Doest et al. IEEE Transactions on Information Technology in Biomedicine, vol. 12, No. 3, May 2008.

Tissue velocity imaging of coronary artery by rotating-type intravascular ultrasound by Saijo et al. Ultrasonics 42 (2004) pp. 753-757.

Official Communication for U.S. Appl. No. 13/239,160 dated Oct. 9, 2013.

Official Communication for U.S. Appl. No. 13/239,160 dated Apr. 14, 2014.

Official Communication for U.S. Appl. No. 13/239,160 dated Aug. 25, 2014.

* cited by examiner

SYSTEMS AND METHODS FOR REDUCING NON-UNIFORM ROTATION DISTORTION IN ULTRASOUND IMAGES

CROSS-REFERENCE TO RELATED APPLICATIONS

This application is a continuation of U.S. patent application Ser. No. 13/239,160 filed Sep. 21, 2011, which issued as U.S. Pat. No. 8,956,299 on Feb. 17, 2015, and which claims the benefit under 35 U.S.C. § 119(e) of U.S. Provisional Patent Application Ser. No. 61/407,854 filed on Oct. 28, 2010, both of which are incorporated herein by reference.

TECHNICAL FIELD

The present invention is directed to the area of imaging systems that are insertable into a patient and methods of making and using the imaging systems. The present invention is also directed to methods and imaging systems for reducing the effects of non-uniform rotation distortion in ultrasound images.

BACKGROUND

Ultrasound devices insertable into patients have proven diagnostic capabilities for a variety of diseases and disorders. For example, intravascular ultrasound ("IVUS") imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety is diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor. In many imaging systems the transducer rotates in order to image the entire vessel. Non-uniform rotation of the transducer may distort the images.

BRIEF SUMMARY

One embodiment is a method for generating an ultrasound image. The method including receiving an image frame comprising consecutive ultrasound scan lines obtained using a rotating ultrasound imaging arrangement and determining at least a first cross-correlation value and a second cross-correlation value for each of a plurality of the scan lines. For each individual scan line of the plurality of scan lines, the first cross-correlation value comprises a cross-correlation coefficient between a first subframe comprising a plurality of consecutive scan lines including the individual scan line and a second subframe comprising a plurality of scan lines shifted from the first subframe by a first integer value. The second correlation value comprising a cross-correlation coefficient between the first subframe and a third subframe comprising a plurality scan lines shifted from the first subframe by a second integer value that is different from the first integer value. The method further includes evaluating, individually for multiple scan lines of the plurality of scan lines, whether the scan line being evaluated exhibits non-uniform rotation distortion using at least one of the first and second correlation values for the scan line being evaluated. A correction for non-uniform rotation distortion is applied using at least one of the first and second correlation values for at least one of the plurality of scan lines. An ultrasound image is generated using at least the plurality of scan lines with the applied correction and the ultrasound image is displayed.

Another embodiment is a computer-readable medium having processor-executable instructions for generating an ultrasound image. The processor-executable instructions when installed onto a device enable the device to perform actions including receiving imaging data comprises consecutive ultrasound scan lines obtained using a rotating ultrasound imaging arrangement; determining at least a first cross-correlation value and a second cross-correlation value for each of a plurality of the scan lines, wherein, for each individual scan line of the plurality of scan lines, the first cross-correlation value comprising a cross-correlation coefficient between a first subframe comprising a plurality of consecutive scan lines including the individual scan line and a second subframe comprising a plurality of scan lines shifted from the first subframe by a first integer value, the second correlation value comprising a cross-correlation coefficient between the first subframe and a third subframe comprising a plurality scan lines shifted from the first subframe by a second integer value that is different from the first integer value; evaluating, individually for multiple scan lines of the plurality of scan lines, whether the scan line being evaluated exhibits non-uniform rotation distortion using at least one of the first and second correlation values for the scan line being evaluated; applying a correction for non-uniform rotation distortion using at least one of the first and second correlation values for at least one of the plurality of scan lines; generating an ultrasound image using at least the plurality of scan lines with the applied correction; and displaying the ultrasound image.

Yet another embodiment is a system for generating ultrasound images. The system includes a catheter and an ultrasound imaging core insertable into the catheter. The ultrasound imaging core includes at least one transducer and is configured and arranged for rotation of at least a portion of the ultrasound imaging core to provide a plurality of radial scan lines. The system also includes a processor that is coupleable to the ultrasound imaging core and is capable of executing processor-readable instructions that enable actions, including: receiving the plurality of scan lines obtained using the ultrasound imaging core; determining at least a first cross-correlation value and a second cross-correlation value for each of a plurality of the scan lines, wherein, for each individual scan line of the plurality of scan lines, the first cross-correlation value comprising a cross-correlation coefficient between a first subframe comprising a plurality of consecutive scan lines including the individual scan line and a second subframe comprising a plurality of scan lines shifted from the first subframe by a first integer value, the second correlation value comprising a cross-correlation coefficient between the first subframe and a third subframe comprising a plurality scan lines shifted from the first subframe by a second integer value that is different from the first integer value; evaluating, individually for multiple scan lines of the plurality of scan lines, whether the scan line being evaluated exhibits non-uniform rotation distortion using at least one of the first and second correlation values for the scan line being evaluated; applying a correction for non-uniform rotation distortion using at least one of the first and second correlation values for at least one of the plurality of scan lines; generating an ultrasound image using at least the plurality of scan lines with the applied correction; and displaying the ultrasound image.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of imaging systems that are insertable into a patient and methods of making and using the imaging systems. The present invention is also directed to methods and imaging systems for reducing the effects of non-uniform rotation distortion in ultrasound images.

The methods, systems, and devices described herein may be embodied in many different forms and should not be construed as limited to the embodiments set forth herein. Accordingly, the methods, systems, and devices described herein may take the form of an entirely hardware embodiment, an entirely software embodiment or an embodiment combining software and hardware aspects. The methods described herein can be performed using any type of computing device, such as a computer, that includes a processor or any combination of computing devices where each device performs at least part of the process.

Suitable computing devices typically include mass memory and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

Methods of communication between devices or components of a system can include both wired and wireless (e.g., RF, optical, or infrared) communications methods and such methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

Suitable intravascular ultrasound ("IVUS") imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,246,959; 7,306,561; and 6,945,938; as well as U.S. Patent Application Publication Nos. 2006/0100522; 2006/0106320; 2006/0173350; 2006/0253028; 2007/0016054; and 2007/0038111; all of which are incorporated herein by reference.

Figure 1:
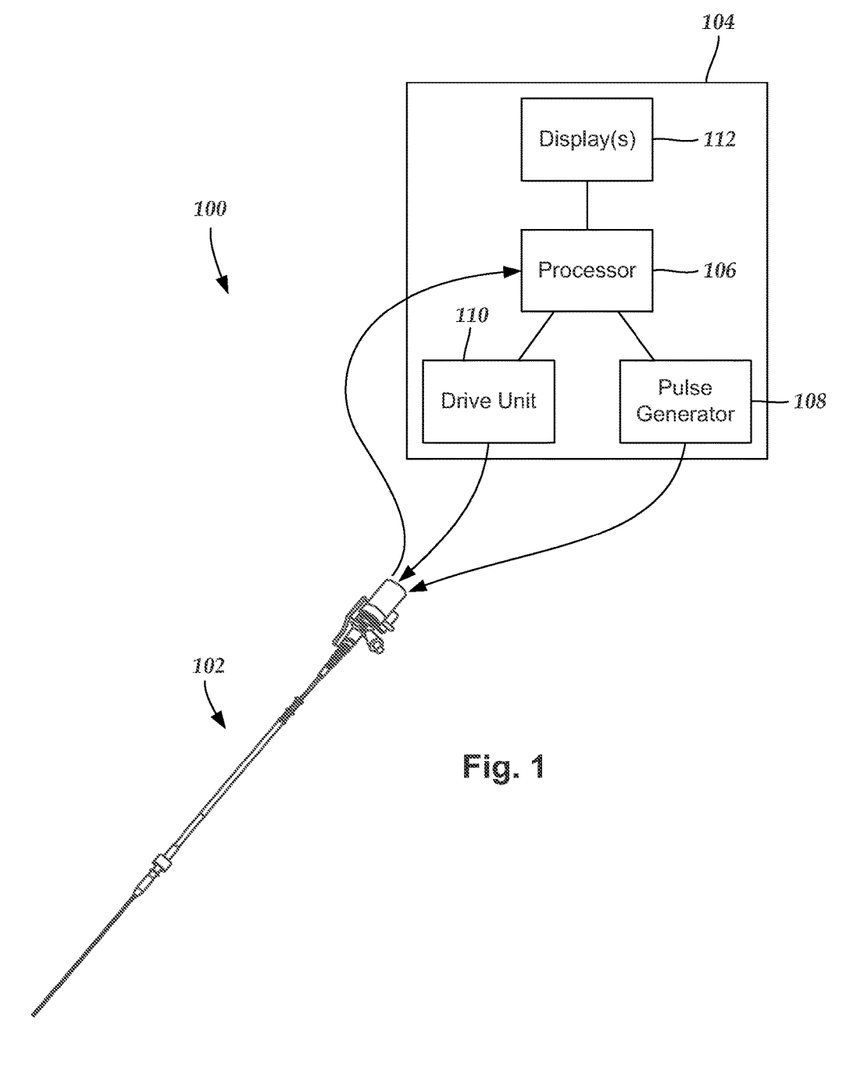
FIG. 1 is a schematic view of one embodiment of an ultrasound imaging system suitable for insertion into a patient, according to the invention.

FIG. 1 illustrates schematically one embodiment of an IVUS imaging system 100. The IVUS imaging system 100 includes a catheter 102 that is coupleable to a control module 104. The control module 104 may include, for example, a processor 106, a pulse generator 108, a drive unit 110, and one or more displays 112. In at least some embodiments, the pulse generator 108 forms electric pulses that may be input to one or more transducers (312 in FIG. 3) disposed in the catheter 102.

In at least some embodiments, mechanical energy from the drive unit 110 may be used to drive an imaging core (306 in FIG. 3) disposed in the catheter 102. In at least some embodiments, electric signals transmitted from the one or more transducers (312 in FIG. 3) may be input to the processor 106 for processing. In at least some embodiments, the processed electric signals from the one or more transducers (312 in FIG. 3) can be displayed as one or more images on the one or more displays 112. For example, a scan converter can be used to map scan line samples (e.g., radial scan line samples, or the like) to a two-dimensional Cartesian grid to display the one or more images on the one or more displays 112.

In at least some embodiments, the processor 106 may also be used to control the functioning of one or more of the other components of the control module 104. For example, the processor 106 may be used to control at least one of the frequency or duration of the electrical pulses transmitted from the pulse generator 108, the rotation rate of the imaging core (306 in FIG. 3) by the drive unit 110, the velocity or length of the pullback of the imaging core (306 in FIG. 3) by the drive unit 110, or one or more properties of one or more images formed on the one or more displays 112.

Figure 2:
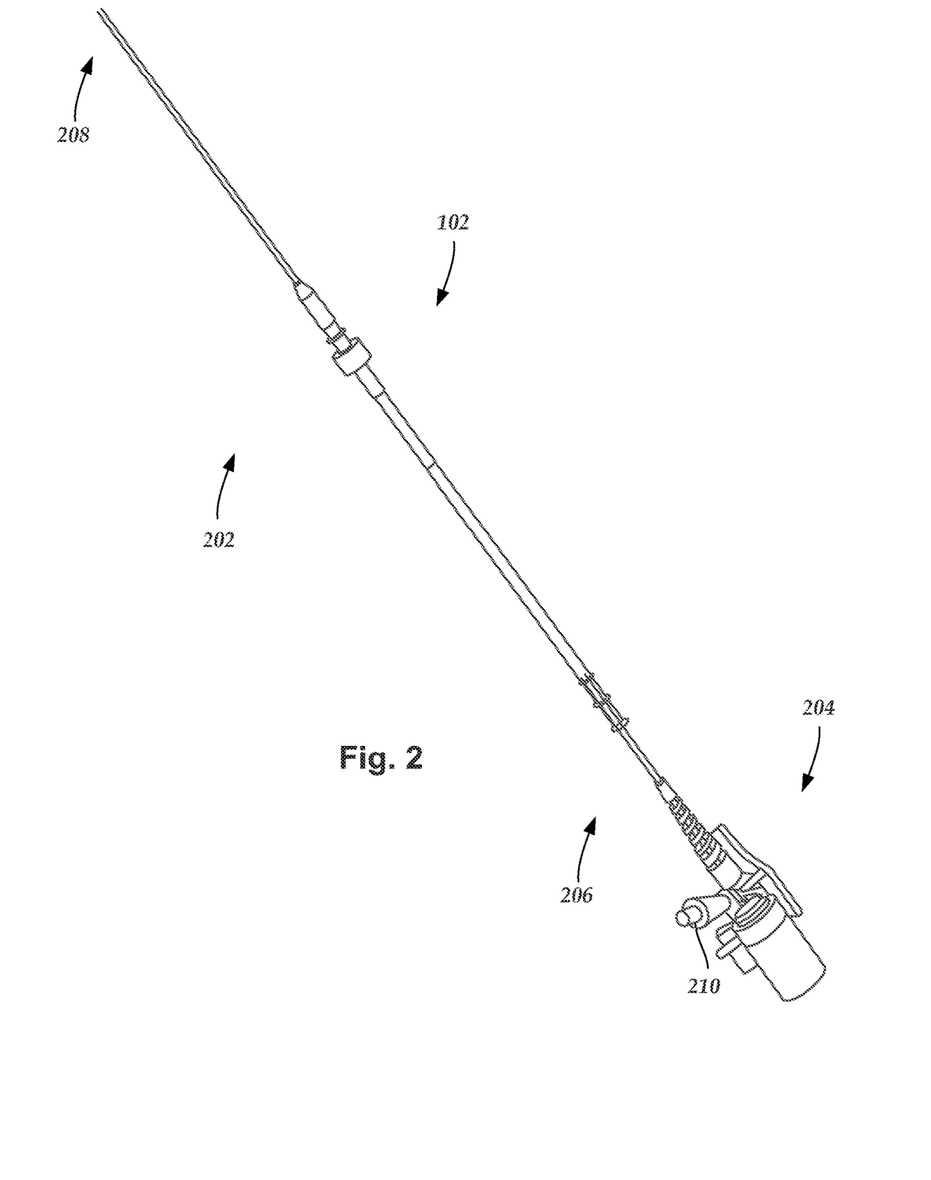
FIG. 2 is a schematic side view of one embodiment of a catheter suitable for use with the ultrasound imaging system of FIG. 1, according to the invention.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2, the proximal end 206 of the elongated member 202 is coupled to the catheter hub 204 and the distal end 208 of the elongated member is configured and arranged for percutaneous insertion into a patient. Optionally, the catheter 102 may define at least one flush port, such as flush port 210. The flush port 210 may be defined in the hub 204. The hub 204 may be configured and arranged to couple to the control module (104 in FIG. 1). In some embodiments, the elongated member 202 and the hub 204 are formed as a unitary body. In other embodiments, the elongated member 202 and the catheter hub 204 are formed separately and subsequently assembled together.

Figure 3:
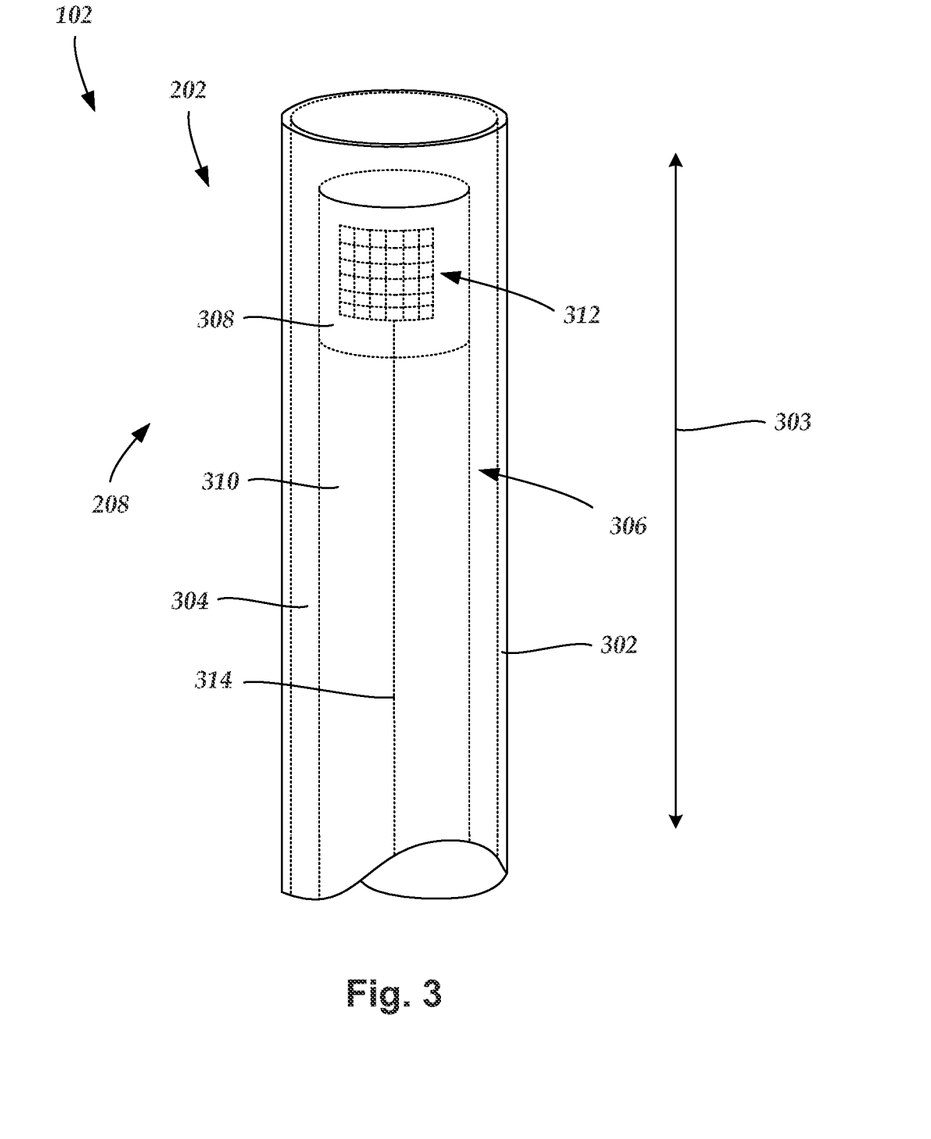
FIG. 3 is a schematic longitudinal cross-sectional view of one embodiment of a distal end of the catheter of FIG. 2 with an imaging core disposed in a lumen defined in a sheath, according to the invention.

FIG. 3 is a schematic perspective view of one embodiment of the distal end 208 of the elongated member 202 of the catheter 102. The elongated member 202 includes a sheath 302 with a longitudinal axis 303 and a lumen 304. An imaging core 306 is disposed in the lumen 304. The imaging core 306 includes an imaging device 308 coupled to a distal end of a driveshaft 310 that is rotatable either manually or using a computer-controlled drive mechanism. One or more transducers 312 may be mounted to the imaging device 308 and employed to transmit and receive acoustic signals. The sheath 302 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

In a preferred embodiment (as shown in FIG. 3), an array of transducers 312 are mounted to the imaging device 308. In alternate embodiments, a single transducer may be employed. Any suitable number of transducers 312 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used. When a plurality of transducers 312 are employed, the transducers 312 can be configured into any suitable arrangement including, for example, an annular arrangement, a rectangular arrangement, or the like.

The one or more transducers 312 may be formed from one or more known materials capable of transforming applied electrical pulses to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like. Other transducer technologies include composite materials, single-crystal composites, and semiconductor devices (e.g., capacitive micromachined ultrasound transducers ("cMUT"), piezoelectric micromachined ultrasound transducers ("pMUT"), or the like)

The pressure distortions on the surface of the one or more transducers 312 form acoustic pulses of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic pulses of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 312 may include a layer of piezoelectric material sandwiched between a conductive acoustic lens and a conductive backing material formed from an acoustically absorbent material (e.g., an epoxy substrate with tungsten particles). During operation, the piezoelectric layer may be electrically excited by both the backing material and the acoustic lens to cause the emission of acoustic pulses.

The one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form an image of the walls of the blood vessel and tissue surrounding the blood vessel.

The imaging core 306 is rotated about the longitudinal axis 303 of the catheter 102. As the imaging core 306 rotates, the one or more transducers 312 emit acoustic signals in different radial directions (i.e., along different radial scan lines). For example, the one or more transducers 312 can emit acoustic signals at regular (or irregular) increments, such as 256 radial scan lines per revolution, or the like. It will be understood that other numbers of radial scan lines can be emitted per revolution, instead.

When an emitted acoustic pulse with sufficient energy encounters one or more medium boundaries, such as one or more tissue boundaries, a portion of the emitted acoustic pulse is reflected back to the emitting transducer as an echo pulse. Each echo pulse that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic pulses transmitted and the echo pulses received. In at least some embodiments, the rotation of the imaging core 306 is driven by the drive unit 110 disposed in the control module (104 in FIG. 1). In alternate embodiments, the one or more transducers 312 are fixed in place and do not rotate. In which case, the driveshaft 310 may, instead, rotate a mirror that reflects acoustic signals to and from the fixed one or more transducers 312.

When the one or more transducers 312 are rotated about the longitudinal axis 303 of the catheter 102 emitting acoustic pulses, a plurality of images can be formed that collectively form a radial cross-sectional image (e.g., a tomographic image) of a portion of the region surrounding the one or more transducers 312, such as the walls of a blood vessel of interest and tissue surrounding the blood vessel. The radial cross-sectional image can, optionally, be displayed on one or more displays 112. The at least one of the imaging core 306 can be either manually rotated or rotated using a computer-controlled mechanism.

The imaging core 306 may also move longitudinally along the blood vessel within which the catheter 102 is inserted so that a plurality of cross-sectional images may be formed along a longitudinal length of the blood vessel. During an imaging procedure the one or more transducers 312 may be retracted (i.e., pulled back) along the longitudinal length of the catheter 102. The catheter 102 can include at least one telescoping section that can be retracted during pullback of the one or more transducers 312. In at least some embodiments, the drive unit 110 drives the pullback of the imaging core 306 within the catheter 102. The drive unit 110 pullback distance of the imaging core can be any suitable distance including, for example, at least 5 cm, 10 cm, 15 cm, 20 cm, 25 cm, or more. The entire catheter 102 can be retracted during an imaging procedure either with or without the imaging core 306 moving longitudinally independently of the catheter 102.

When the imaging core 306 is refracted while rotating, the images may collectively form a continuous spiral shape along a blood vessel. A stepper motor may, optionally, be used to pull back the imaging core 306. The stepper motor can pull back the imaging core 306 a short distance and stop long enough for the one or more transducers 306 to capture an image or series of images before pulling back the imaging core 306 another short distance and again capturing another image or series of images, and so on.

The quality of an image produced at different depths from the one or more transducers 312 may be affected by one or more factors including, for example, bandwidth, transducer focus, beam pattern, as well as the frequency of the acoustic pulse. The frequency of the acoustic pulse output from the one or more transducers 312 may also affect the penetration depth of the acoustic pulse output from the one or more transducers 312. In general, as the frequency of an acoustic pulse is lowered, the depth of the penetration of the acoustic pulse within patient tissue increases. In at least some embodiments, the IVUS imaging system 100 operates within a frequency range of 5 MHz to 100 MHz.

One or more conductors 314 can electrically couple the transducers 312 to the control module 104 (see e.g., FIG. 1). In which case, the one or more conductors 314 may extend along a longitudinal length of the rotatable driveshaft 310.

The catheter 102 with one or more transducers 312 mounted to the distal end 208 of the imaging core 308 may be inserted percutaneously into a patient via an accessible blood vessel, such as the femoral artery, femoral vein, or jugular vein, at a site remote from the selected portion of the selected region, such as a blood vessel, to be imaged. The catheter 102 may then be advanced through the blood vessels of the patient to the selected imaging site, such as a portion of a selected blood vessel.

As indicated above, the transducer(s) or a mirror is typically rotated during operation. As the transducer(s) or mirror rotates, the transducer(s) is pulsed to emit acoustic energy. The transducer(s) then receives the reflected acoustic energy. During this reception period, the transducer(s) or mirror may be stationary or rotating. The received acoustic energy between two pulses can be referred to a as a scan line. Each scan line typically includes a number of points that represent reception of the reflected acoustic energy over time and are generally correlated with depth. In at least some embodiments, the number of scan lines per revolution is at least 64, 100, 128, 200, 256, 300, 400, 500, 512, 1000, or 1028.

Figure 4:
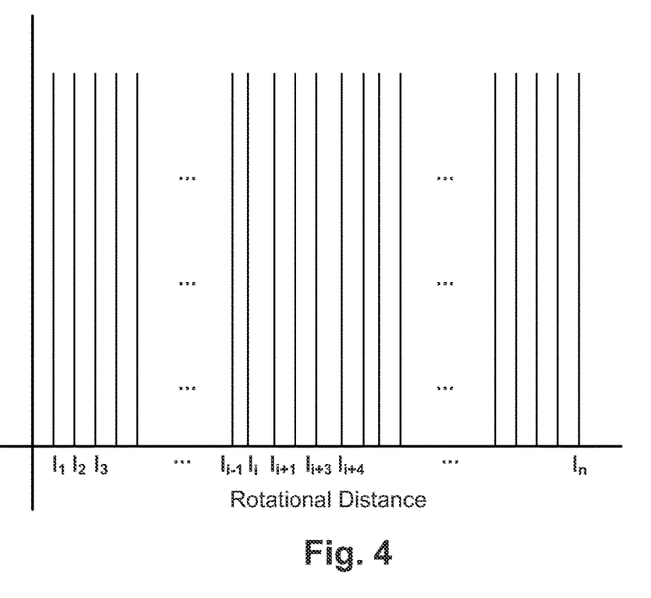
FIG. 4 is a schematic diagram illustrating spacing of scan lines.

Ideally, the scan lines are spaced an equal distance apart. Equal spacing of the scan lines can be obtained by uniform rotation. If the rotation is non-uniform, then the spacing between the scan lines will also be non-uniform. Such non-uniformity can result in what is often referred to as non-uniform rotation distortion (NURD) and can produce distortion in the ultrasound image. FIG. 4 schematically illustrates the concept of non-uniform rotation by graphing each scan line, $l_1, l_2, \ldots, l_n$ versus rotational distance (x-axis). The y-axis corresponds to the sample points for each scan line. In FIG. 4, scan lines $l_1$, $l_2$, and $l_3$ are equally spaced apart indicating uniform rotation. In contrast, lines $l_{i-1}$ and $l_i$ are closer together, indicating that the rotational speed of the transducer(s) or mirror may have slowed. Lines $l_i$ and $l_{i+1}$ and lines $l_{i+3}$ and $l_{i+4}$ are further apart indicating that the rotational speed of the transducer(s) or mirror may have increased.

The scan lines and associated data can be examined and the presence of non-uniform rotation distortion can be observed and at least partially corrected. Although the correction of non-uniform rotation distortion is described herein in the context of ultrasound imaging, it will be understood that this correction can also be applied to other imaging techniques that utilize rotating imaging receivers, such as optical coherence tomography.

Figure 5:
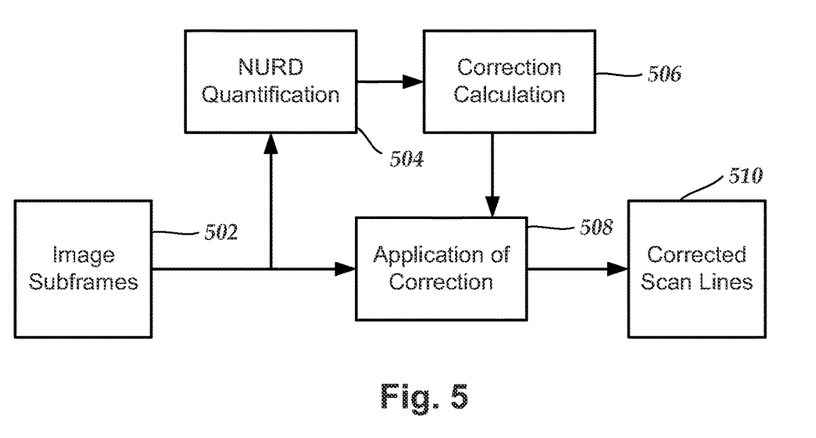
FIG. 5 is a schematic block diagram illustrating one embodiment of a method for at least partially correcting for non-uniform rotation distortion, according to the invention.

FIG. 5 is a block diagram illustrating schematically one embodiment of a procedure for at least partially correcting non-uniform rotation distortion (NURD). The level of NURD around each scan line L in the image frame can be calculated through cross-correlation values between image subframes. Image subframes are selected from the image frame (box 502). As an example, for each image frame $F(r,L)$ that includes $L_T$ scan lines with each scan line containing $r_T$ sample points, image subframes are selected with each subframe including a number $\Delta_L$ of consecutive scan lines distributed around, and including, a scan line, L, and a range $[r_1, r_2]$ of consecutive sample points from each scan line distributed around, and including, a sample point, r. It will be understood that the imaging data in the image frame can be the radio-frequency (RF) data directly from the transducer or data that has been at least partially processed (e.g., data with filtering, amplitude detection, log-compression or other non-linear mapping of amplitudes). The image frames can be averaged over consecutive acquisitions of ultrasound data.

The total number of scan lines, $\Delta_1$, in a subframe can be two, three, four, five, six, seven, eight, nine, ten, eleven, twelve, or more. Preferably, the scan lines of the subframe are symmetrically selected about the particular scan line, L, which would result in $\Delta_L$ being an odd number (e.g., three, five, seven, nine, eleven, etc.)

The number of sample points per scan line in the range $[r_1, r_2]$ of the subframe is preferably at least one-eighth of the total number of sample points in the scan line and can be at least one-quarter, one-half, two-thirds, three-quarters, or even all of the sample points of the scan line. It will be understood that each scan line may have the same number of sample points or may have differing numbers of sample points.

In some embodiments, the level of NURD is estimated around each scan line in the image frame, therefore all scan lines in an image frame are selected for calculation. Alternatively, the level of NURD is estimated for only a portion of the scan lines (e.g., every other scan line or every third scan line), thus a subset of scan lines are selected for calculation.

The presence or absence of non-uniform rotation distortion (NURD) is then determined (box 504) for each selected scan line from the image frame. This determination includes calculating two or more cross-correlation values between nearby subframes for each selected line. In at least some embodiments, the subframe cross-correlation values are calculated between the subframe that includes the selected scan line and another subframe that may or may not includes that line.

Each subframe cross-correlation value is calculated between a subframe and another subframe that corresponds to the original subframe shifted by an integer number, $\delta_L$, of scan lines. For a particular subframe, each calculated cross-correlation value is for a different value of $\delta_L$. The integer number $\delta_L$ can be any suitable integer value such as one, two, three, four, five, six, seven, eight, or more and can be positive or negative.

One example of a cross-correlation value $C(L;\delta_L)$ is given by the following equation:

$$C(L;\delta_L) = \frac{\sum_{L'=-(\Delta_L-1)/2}^{(\Delta_L-1)/2} \sum_{r=r_1}^{r_2} (F(r, L+L') - \overline{F}(L)) \cdot (F(r, L+\delta_L+L') - \overline{F}(L+\delta_L))}{\sqrt{\sum_{L'=-(\Delta_L-1)/2}^{(\Delta_L-1)/2} \sum_{r=r_1}^{r_2} (F(r, L+L') - \overline{F}(L))^2} \cdot \sqrt{\sum_{L'=-(\Delta_L-1)/2}^{(\Delta_L-1)/2} \sum_{r=r_1}^{r_2} (F(r, L+\delta_L+L') - \overline{F}(L+\delta_L))^2}}$$

where $\overline{F}(L) = \frac{1}{\Delta_L \cdot (r_2 - r_1)} \cdot \sum_{L'=-(\Delta_L-1)/2}^{(\Delta_L-1)/2} \sum_{r=r_1}^{r_2} (F(r, L+L'))$.

In this instance, the cross-correlation values have been normalized. Alternatively, i) the cross-correlation values are not normalized, ii) the cross-correlation values are calculated without subtracting the mean values (e.g., $\overline{F}(L)$ and $\overline{F}(L+\delta_L)$), or iii) a combination of i) and ii).

These cross-correlation values are functions of both the lateral resolution of the imaging system and the rotation distortion. To separate the rotation distortion effects on the cross-correlation values from that of image resolution, the relative cross-correlation values, $CR(L;\delta_L)$, can be calculated by normalizing $C(L;\delta_L)$ with its average over the whole or a nearby portion of the image frame, $$CR(L;\delta_L) \equiv \frac{(2D+1) \cdot C(L;\delta_L)}{\sum_{L'=-D}^{D} C(L+L'; \delta_L)}$$

where $2D+1 < L_T$, the total number of scan lines in the frame or the selected portion of the frame.

As an example, the cross-correlation values $CR(L;1)$ and $CR(L;3)$ for each selected line can be calculated. Individual scan lines within an image frame can be identified as demonstrating non-uniform rotation distortion based on a selected threshold condition of the subframe cross-correlation values. As an example, a threshold condition could be that non-uniform rotation distortion is indicated if one or more, or if a specific one, of the subframe cross-correlation values are outside of a threshold range. For example, it will be expected that image lines without non-uniform rotation distortion will have $CR(L,1) \cong =1$. Image lines with $CR(L;1)$ outside a threshold range around 1 will indicate the likely presence of non-uniform rotation distortion. For other cross-correlation values (e.g., $CR(L;3)$) the expected value will likely not be 1, but could be another number (for example, an average or median value for the imaging data). Any suitable threshold range and threshold values can be used and the threshold range may be symmetrical or asymmetrical about the value of expected value (e.g., 1 for $CR(L;1)$). For example, the threshold range may be from 1−t to 1+t where t is any suitable value less than 1. The value t may be at least 0.05, 0.1, 0.15, 0.2, 0.25, or more.

Figure 6:
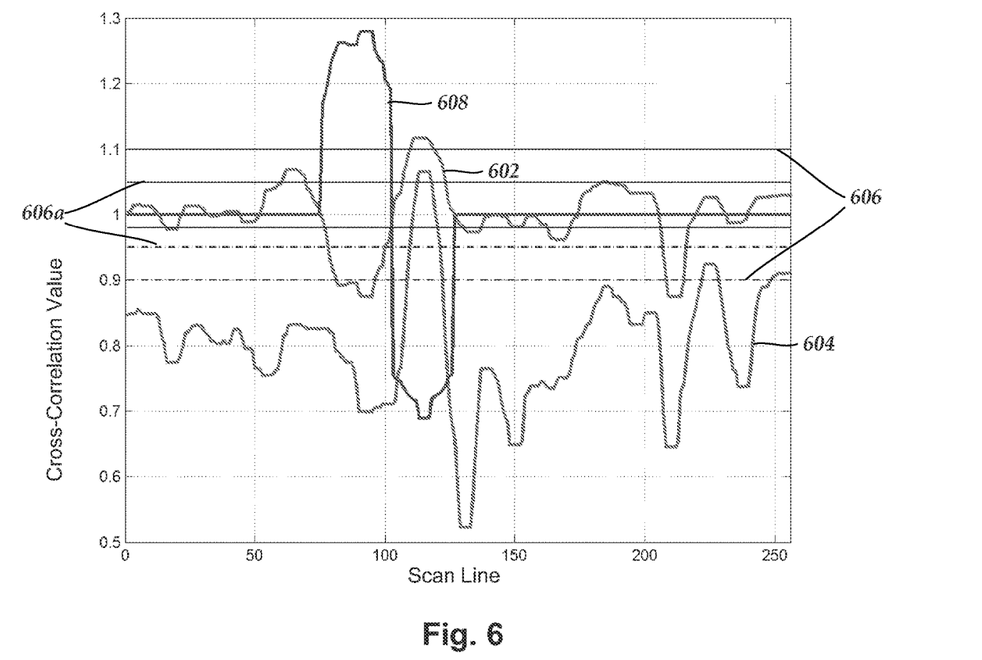
FIG. 6 is a graph of cross-correlation values and one embodiment of a scan line correction for a set of scan lines, according to the invention.

FIG. 6 is a graph of $CR(L;1)$ 602 and $CR(L;3)$ 604 for one set of data. Also illustrated are threshold values 606. Values of $CR(L;1)$ outside this range may be considered to indicate non-uniform rotation distortion. Alternative threshold values 606a are also illustrated. In some embodiments, one cross-correlation value (e.g. $CR(L;1)$) is used to determine the likelihood of non-uniform rotation distortion and a second cross-correlation value (e.g., $CR(L;3)$) is used to confirm that determination.

In at least some embodiments, only portions of the image frame that are determined to likely demonstrate non-uniform rotation distortion will be corrected. In other embodiments, those portions, as well as adjacent portions of the data, will be corrected. In yet other embodiments, all of the image frame will be corrected.

Figure 7:
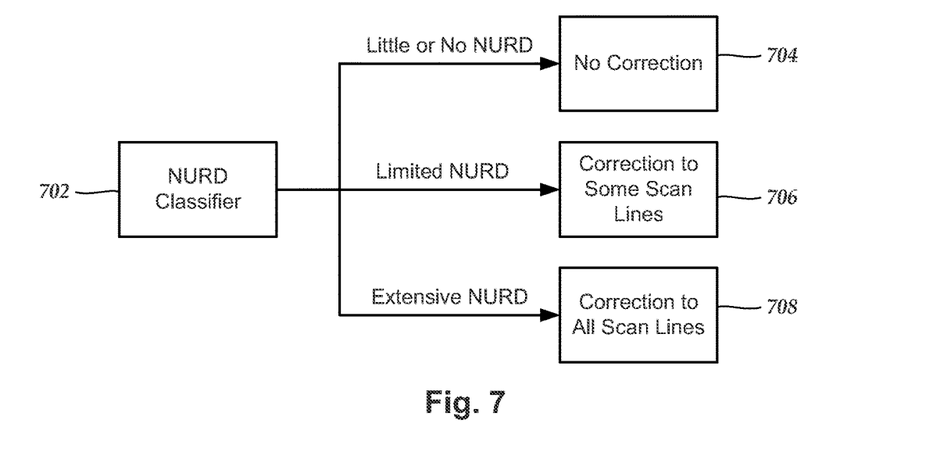
FIG. 7 is a schematic block diagram illustrating one embodiment of a method for classifying the amount of correction to be applied to a set of imaging data.

In some embodiments, the portion of the image frame that will be corrected can depend on the relative amount of non-uniform rotation distortion (NURD) identified within the image frame. FIG. 7 illustrates in a block diagram one embodiment of a procedure for determining which portions of the image frame will be corrected. A NURD classifier 702 evaluates the cross-correlation values for the image frames. If there is little or no NURD present in the image frame, then no NURD correction is applied (box 704). If it is determined that NURD is likely present in a limited region or regions of frame, the NURD correction is applied to those regions (and optionally to adjacent regions) (box 706). If there is extensive NURD in the image frame, then NURD correction is applied to the entire set of frame (box 708). It will be understood that the thresholds between the three conditions (e.g., the threshold between when no NURD correction is applied and when NURD correction is applied regionally, or the threshold between when regional NURD correction is applied and when global NURD correction is applied) can be selected to be any suitable values and may depend on the imaging application or setting or may be set by a user.

Returning to FIG. 5, a correction for one or more regions or, in some embodiments, for the entire image frame can be determined (box 506). FIG. 6 illustrates a scan line correction 608 that is applied to only some scan lines. A correction can be calculated for each scan line to be corrected. The correction may be a line spacing correction that interpolates a corrected scan line from lines adjacent the scan line to be corrected. Alternatively, the correction may include a determination of the actual coordinates of one or more of the scan lines.

One example of a scan line correction, s(L), for a scan line, L, has the following form:
s(L)=k/CR(L;1) when CR(L;1)≤1;
s(L)=k/2 when CR(L;1)>1 and $C_s$≤0;
s(L)=k/2/(1+$C_s$) when CR(L;1)>1 and $C_s$>0, where
k is a scaling constant;
$C_s$=($C_{3thresh}$−CR(L;3))/(CR(L;3)−CR(L;1))   where $C_{3thresh}$ is a threshold level selected for CR(L;3). For example, $C_{3thresh}$ can be 1.10, 1.05, 1.00, or 0.95.

The scaling constant k can be one or may be selected for normalization with respect to the entire set of imaging data or may be selected for normalization with respect to only a portion of the imaging data including the scan line, L. In some embodiments, the scaling constant, k, may be different for each scan line and vary based on the degree to which one or more of the cross-correlation values for that scan line are outside of the threshold range.

For a smoother frame to frame transition, s(L) can be smoothed over consecutive image frames. For example, for frame n with scan line correction $s_n(L)$, the smoothed correction for frame n becomes,
$s'_n(L) = \alpha s_{n-1}(L) + (1-\alpha) s_n(L)$, where α<1 is a weighting constant.
In a more general form, $$s'_n(L) = \sum_{n'=-\Delta_1}^{\Delta_2} \alpha_{n'} s_{n+n'}(L), \text{ where } \sum_{n=\Delta_1}^{\Delta_2} \alpha_n = 1$$

and $\Delta_1$ and $\Delta_2$ are integers and can be the same or different.

In another embodiment, a modified scan line correction, $s_T(L)$, can be determined for all or some of the scan lines. The modified scan line correction can include the scan line correction, s(L), and a global scan line correction, $s_g(L)$, that are combined in a weighted arrangement.

As an example,
$s_T(L)=\beta s(L)+(1-\beta)s_g(L)$, where s(L) is calculated as described above;
$s_g(L)=k_g/C(L;1)$ when C(L;1)≤1;
$s_g(L)=k_g/2$ when C(L;1)>1 and $C_s$≤0;
$s_g(L)=k_g/2/(1+C_s)$ when C(L;1)>1 and $C_s$>0, where
$k_g$ is a scaling constant; and
β is a weighting constant that is between 0 and 1.

The scan line correction s(L) (or s'(L) or $s_T(L)$) can be made to each scan line that is to be corrected (box 508) to give a corrected scan lines/frames (box 510). In some embodiments, the scan line correction, s(L) (or s'(L) or $s_T(L)$), can be applied to each scan line for which NURD is likely determined. In other embodiments, the scan line correction, s(L) (or s'(L) or $s_T(L)$), is applied to every scan line.

The corrected scan lines can then be processed using any know processing method to yield one or more images (e.g., ultrasound images). The corrections to the scan lines should improve the quality of the images.

It will be understood that each block of the block diagram illustrations, and combinations of blocks in the block diagram illustrations, as well any portion of the systems and methods disclosed herein, can be implemented by computer program instructions. These program instructions may be provided to a processor to produce a machine, such that the instructions, which execute on the processor, create means for implementing the actions specified in the block diagram block or blocks or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method for generating an ultrasound image, the method comprising:
   receiving an image frame comprising a plurality of consecutive ultrasound scan lines obtained using a rotating ultrasound imaging arrangement;
   determining at least a first cross-correlation value and a second cross-correlation value for each of a plurality of the scan lines, wherein, for each individual scan line of the plurality of scan lines, the first cross-correlation value comprising a cross-correlation coefficient between a first subframe comprising a plurality of consecutive scan lines including the individual scan line and a second subframe comprising a plurality of scan lines shifted from the first subframe by a number of scan lines equal to a first integer value, the second cross-correlation value comprising a cross-correlation coefficient between the first subframe and a third subframe comprising a plurality of scan lines shifted from the first subframe by a number of scan lines equal to a second integer value that is different from the first integer value, wherein the first and second integer values are positive integer values;
   evaluating, individually for multiple scan lines of the plurality of scan lines, whether the scan line being evaluated exhibits non-uniform rotation distortion using at least one of the first and second cross-correlation values for the scan line being evaluated;
   determining a correction for non-uniform rotation distortion for at least a one of the plurality of scan lines using at least one of the first and second cross-correlation values determined for the one of the plurality of scan lines;
   generating the ultrasound image using at least the plurality of scan lines with the determined correction; and
   displaying the ultrasound image.

2. The method of claim 1, wherein the first cross-correlation value and the second cross-correlation value are normalized.

3. The method of claim 1, wherein the first integer value is one.

4. The method of claim 3, wherein the second integer value is two.

5. The method of claim 1, wherein the image frame comprises image frame F(r,L) where L is a scan line in the image frame and r is a sample point of the scan line in the image frame, the first subframe includes $\Delta_L$ scan lines around a particular scan line L and sample points in the range of $[r_1,r_2]$ and the first cross-correlation value is C(L, $\delta_L$), wherein $\delta_L$ is the first integer value to be used for determining the first cross-correlation value, and $$C(L, \delta_L) = \frac{\sum_{L'=-(\Delta_L-1)/2}^{(\Delta_L-1)/2} \sum_{r=r_1}^{r_2} (F(r, L+L') - \overline{F}(L)) \cdot (F(r, L+\delta_L+L') - \overline{F}(L+\delta_L))}{\sqrt{\sum_{L'=-(\Delta_L-1)/2}^{(\Delta_L-1)/2} \sum_{r=r_1}^{r_2} (F(r, L+L') - \overline{F}(L))^2} \cdot \sqrt{\sum_{L'=-(\Delta_L-1)/2}^{(\Delta_L-1)/2} \sum_{r=r_1}^{r_2} (F(r, L+\delta_L+L') - \overline{F}(L+\delta_L))^2}}$$

wherein $\overline{F}(L) = \frac{1}{\Delta_L \cdot (r_2 - r_1)} \cdot \sum_{L'=-(\Delta_L-1)/2}^{(\Delta_L-1)/2} \sum_{r=r_1}^{r_2} (F(r, L+L'))$.

6. The method of claim 1, wherein the image frame comprises image frame F(r,L) where L is a scan line in the image frame and r is a sample point of the scan line in the image frame, the first subframe includes $\Delta_L$ scan lines around a particular scan line L and sample points in the range of $[r_1,r_2]$ and the first cross-correlation value is CR(L, $\delta_L$), wherein $\delta_L$ is the first integer value to be used for determining the first cross-correlation value, wherein $$CR(L; \delta_L) \equiv \frac{(2D+1) \cdot C(L; \delta_L)}{\sum_{L'=-D}^{D} C(L+L'; \delta_L)},$$

wherein $2D+1 < \Delta_L$ and $$C(L, \delta_L) = \frac{\sum_{L'=-(\Delta_L-1)/2}^{(\Delta_L-1)/2} \sum_{r=r_1}^{r_2} (F(r, L+L') - \overline{F}(L)) \cdot (F(r, L+\delta_L+L') - \overline{F}(L+\delta_L))}{\sqrt{\sum_{L'=-(\Delta_L-1)/2}^{(\Delta_L-1)/2} \sum_{r=r_1}^{r_2} (F(r, L+L') - \overline{F}(L))^2} \cdot \sqrt{\sum_{L'=-(\Delta_L-1)/2}^{(\Delta_L-1)/2} \sum_{r=r_1}^{r_2} (F(r, L+\delta_L+L') - \overline{F}(L+\delta_L))^2}}$$

wherein $\overline{F}(L) = \frac{1}{\Delta_L \cdot (r_2 - r_1)} \cdot \sum_{L'=-(\Delta_L-1)/2}^{(\Delta_L-1)/2} \sum_{r=r_1}^{r_2} (F(r, L+L'))$.

7. The method of claim 6, wherein the first cross-correlation value is CR(L,1) and the second cross-correlation value is CR(L,3).

8. The method of claim 7, wherein the correction for non-uniform rotation for the scan line L is:
s(L)=k/CR(L,1) when CR(L,1)≤1;
s(L)=k/2 when CR(L,1)>1 and $C_s$≤0;
s(L)=k/2/(1+$C_s$) when CR(L,1)>1 and $C_s$>0;
wherein k is a scaling constant; and
$C_s$=($C_{3thresh}$−CR(L,3))/(CR(L,3)−CR(L,1)) wherein $C_{3thresh}$ is a threshold level selected for CR(L,3).

9. The method of claim 7, wherein the correction for non-uniform rotation for the scan line L in an n-th image frame is $s'_n(L)=\alpha s_{n-1}(L)+(1-\alpha)s_n(L)$, where $\alpha<1$, is a weighting constant and an unsmoothed scan line correction $s_n(L)$, defined in the n-th image frame, is
$s_n(L)$=k/CR(L,1) when CR(L,1)≤1;
$s_n(L)$=k/2 when CR(L,1)>1 and $C_s$≤0;
$s_n(L)$=k/2/(1+$C_s$) when CR(L,1)>1 and $C_s$>0;
wherein k is a scaling constant; and
$C_s$=($C_{3thresh}$−CR(L,3))/(CR(L,3)−CR(L,1)) wherein $C_{3thresh}$ is a threshold level selected for CR(L,3).

10. The method of claim 7, wherein the correction for non-uniform rotation for the scan line L in an n-th image frame is $$s'_n(L) = \sum_{n'=-\Delta_1}^{\Delta_2} \alpha_{n'} s_{n+n'}(L), \text{ wherein } \sum_{n=\Delta_1}^{\Delta_2} \alpha_n = 1$$

and $\Delta_1$ and $\Delta_2$ are integers and can be the same or different, and an unsmoothed scan line correction $s_n(L)$, defined in the n-th image frame, is
$s_n(L)$=k/CR(L,1) when CR(L,1)≤1;
$s_n(L)$=k/2 when CR(L,1)>1 and $C_s$≤0;
$s_n(L)$=k/2/(1+$C_s$) when CR(L,1)>1 and $C_s$>0;
wherein k is a scaling constant; and
$C_s$=($C_{3thresh}$−CR(L,3))/(CR(L,3)−CR(L,1)) wherein $C_{3thresh}$ is a threshold level selected for CR(L,3).

11. The method of claim 7, wherein the correction for non-uniform rotation for the scan line L is:
$s_T(L)=\beta s(L)+(1-\beta)s_g(L)$,
wherein
s(L)=k/CR(L,1) when CR(L,1)≤1;
s(L)=k/2 when CR(L,1)>1 and $C_s$≤0;
s(L)=k/2/(1+$C_s$) when CR(L,1)>1 and $C_s$>0;
k is a first scaling constant;
$C_s$=($C_{3thresh}$−CR(L,3))/(CR(L,3)−CR(L,1)) wherein $C_{3thresh}$ is a threshold level selected for CR(L,3);
$s_g(L)=k_g/C(L;1)$ when C(L;1)≤1;
$s_g(L)=k_g/2$ when C(L;1)>1 and $C_s$≤0;
$s_g(L)=k_g/2/(1+C_s)$ when C(L;1)>1 and $C_s$>0;
$k_g$ is a second scaling constant; and
$\beta$ is a weighting constant that is between 0 and 1.

12. A non-transitory computer-readable medium having processor-executable instructions for generating an ultrasound image, the processor-executable instructions when installed onto a device enable the device to perform actions, comprising:
receiving an image frame comprising a plurality of consecutive ultrasound scan lines obtained using a rotating ultrasound imaging arrangement;
determining at least a first cross-correlation value and a second cross-correlation value for each of a plurality of the scan lines, wherein, for each individual scan line of the plurality of scan lines, the first cross-correlation value comprising a cross-correlation coefficient between a first subframe comprising a plurality of consecutive scan lines including the individual scan line and a second subframe comprising a plurality of scan lines shifted from the first subframe by a number of scan lines equal to a first integer value, the second cross-correlation value comprising a cross-correlation coefficient between the first subframe and a third subframe comprising a plurality of scan lines shifted from the first subframe by a number of scan lines equal to a second integer value that is different from the first integer value, wherein the first and second integer values are positive integer values;

evaluating, individually for multiple scan lines of the plurality of scan lines, whether the scan line being evaluated exhibits non-uniform rotation distortion using at least one of the first and second cross-correlation values for the scan line being evaluated;

determining a correction for non-uniform rotation distortion for at least a one of the plurality of scan lines using at least one of the first and second cross-correlation values determined for the one of the plurality of scan lines;

generating the ultrasound image using at least the plurality of scan lines with the determined correction; and displaying the ultrasound image.

13. The non-transitory computer-readable medium of claim 12 wherein the image frame comprises image frame $F(r,L)$ where L is a scan line in the image frame and r is a sample point of the scan line in the image frame, the first subframe includes $\Delta_L$ scan lines around a particular scan line L and sample points in the range of $[r_1, r_2]$ and the first cross-correlation value is $CR(L, \delta_L)$, wherein $\Delta_L$ is the first integer value to be used for determining the first cross-correlation value, and $$CR(L; \delta_L) \equiv \frac{(2D+1) \cdot C(L; \delta_L)}{\sum_{L'=-D}^{D} C(L+L'; \delta_L)}, \text{ wherein } 2D+1 < \Delta_L \text{ and}$$

$$C(L, \delta_L) = \frac{\sum_{L'=-(\Delta_L-1)/2}^{(\Delta_L-1)/2} \sum_{r=r_1}^{r_2} (F(r, L+L') - \overline{F}(L)) \cdot (F(r, L+\delta_L+L') - \overline{F}(L+\delta_L))}{\sqrt{\sum_{L'=-(\Delta_L-1)/2}^{(\Delta_L-1)/2} \sum_{r=r_1}^{r_2} (F(r, L+L') - \overline{F}(L))^2} \cdot \sqrt{\sum_{L'=-(\Delta_L-1)/2}^{(\Delta_L-1)/2} \sum_{r=r_1}^{r_2} (F(r, L+\delta_L+L') - \overline{F}(L+\delta_L))^2}}$$

wherein $\overline{F}(L) = \frac{1}{\Delta_L \cdot (r_2 - r_1)} \cdot \sum_{L'=-(\Delta_L-1)/2}^{(\Delta_L-1)/2} \sum_{r=r_1}^{r_2} (F(r, L+L'))$.

14. The non-transitory computer-readable medium of claim 13, wherein the first cross-correlation value is $CR(L,1)$ and the second cross-correlation value is $CR(L,3)$.

15. The non-transitory computer-readable medium of claim 14, wherein the correction for non-uniform rotation for the scan line L is:

$s(L)=k/CR(L,1)$ when $CR(L,1) \leq 1$;
$s(L)=k/2$ when $CR(L,1)>1$ and $C_s \leq 0$;
$s(L)=k/2/(1+C_s)$ when $CR(L,1)>1$ and $C_s \geq 0$;
wherein k is a scaling constant; and
$C_s = (C_{3thesh} - CR(L,3))/(CR(L,3) - CR(L,1))$ wherein $C_{3thresh}$ is a threshold level selected for $CR(L,3)$.

16. The non-transitory computer-readable medium of claim 14, wherein the correction for non-uniform rotation for the scan line L in an n-th image frame is $s'_n(L) = \alpha s_{n-1}(L) + (1-\alpha)s_n(L)$, where $\alpha<1$ is a weighting constant and an unsmoothed scan line correction $s_n(L)$, defined in the n-th image frame, is $s_n(L)=k/CR(L,1)$ when $CR(L,1) \leq 1$;
$s_n(L)=k/2$ when $CR(L,1)>1$ and $C_s \leq 0$;
$s_n(L)=k/2/(1+C_s)$ when $CR(L,1)>1$ and $C_s > 0$;
wherein k is a scaling constant; and
$C_s = (C_{3thresh} - CR(L,3))/(CR(L,3) - CR(L,1))$ wherein $C_{3thresh}$ is a threshold level selected for $CR(L,3)$.

17. The non-transitory computer-readable medium of claim 14, wherein the correction for non-uniform rotation for the scan line L in an n-th image frame is $$s'_n(L) = \sum_{n'=-\Delta_1}^{\Delta_2} \alpha_{n'} s_{n+n'}(L), \text{ wherein } \sum_{n=\Delta_1}^{\Delta_2} \alpha_n = 1$$

and $\Delta_1$ and $\Delta_2$ are integers and can be the same or different, and an unsmoothed scan line correction $s_n(L)$, defined in the n-th image frame, is $s_n(L)=k/CR(L,1)$ when $CR(L,1) \leq 1$;
$s_n(L)=k/2$ when $CR(L,1)>1$ and $C_s \leq 0$;
$s_n(L)=k/2/(1+C_s)$ when $CR(L,1)>1$ and $C_s > 0$;
wherein k is a scaling constant; and
$C_s = (C_{3thresh} - CR(L,3))/(CR(L,3) - CR(L,1))$ wherein $C_{3thresh}$ is a threshold level selected for $CR(L,3)$.

18. The non-transitory computer-readable medium of claim 14, wherein the correction for non-uniform rotation for the scan line L is:

$s_T(L) = \beta s(L) + (1-\beta)s_g(L)$,
wherein
$s(L)=k/CR(L,1)$ when $CR(L,1) \leq 1$;
$s(L)=k/2$ when $CR(L,1)>1$ and $C_s \leq 0$;
$s(L)=k/2/(1+C_s)$ when $CR(L,1)>1$ and $C_s > 0$;
k is a first scaling constant;
$C_s = (C_{3thresh} - CR(L,3))/(CR(L,3) - CR(L,1))$ wherein $C_{3thresh}$ is a threshold level selected for $CR(L,3)$;
$s_g(L)=k_g/C(L;1)$ when $C(L;1) \leq 1$;
$s_g(L)=k_g/2$ when $C(L;1)>1$ and $C_s \leq 0$;
$s_g(L)=k_g/2/(1+C_s)$ when $C(L;1)>1$ and $C_s > 0$;
$k_g$ is a second scaling constant; and
$\beta$ is a weighting constant that is between 0 and 1.

19. A system for generating an ultrasound image, comprising:
a catheter;
an ultrasound imaging core insertable into the catheter, the ultrasound imaging core comprising at least one transducer and configured and arranged for rotation of at least a portion of the ultrasound imaging core to provide a plurality of radial scan lines;
a processor, coupleable to the ultrasound imaging core, for executing processor-readable instructions that enable actions, including:
receiving an image frame comprising a plurality of consecutive ultrasound scan lines obtained using the rotating ultrasound imaging core;

determining at least a first cross-correlation value and a second cross-correlation value for each of a plurality of the scan lines, wherein, for each individual scan line of the plurality of scan lines, the first cross-correlation value comprising a cross-correlation coefficient between a first subframe comprising a plurality of consecutive scan lines including the individual scan line and a second subframe comprising a plurality of scan lines shifted from the first subframe by a number of scan lines equal to a first integer value, the second cross-correlation value comprising a cross-correlation coefficient between the first subframe and a third subframe comprising a plurality of scan lines shifted from the first subframe by a number of scan lines equal to a second integer value that is different from the first integer value, wherein the first and second integer values are positive integer values;

evaluating, individually for multiple scan lines of the plurality of scan lines, whether the scan line being evaluated exhibits non-uniform rotation distortion using at least one of the first and second cross-correlation values for the scan line being evaluated;

determining a correction for non-uniform rotation distortion for at least a one of the plurality of scan lines using at least one of the first and second cross-correlation values determined for the one of the plurality of scan lines;

generating the ultrasound image using at least the plurality of scan lines with the determined correction; and displaying the ultrasound image.

20. The system of claim 19, wherein the image frame comprises image frame $F(r,L)$ where $L$ is a scan line in the image frame and $r$ is a sample point of the scan line in the image frame, the first subframe includes $\Delta_L$ scan lines around a particular scan line $L$ and sample points in the range of $[r_1, r_2]$ and the first cross-correlation value is $CR(L, \delta_L)$, wherein $\delta_L$ is the first integer value to be used for determining the first cross-correlation value, and $$CR(L; \delta_L) \equiv \frac{(2D+1) \cdot C(L; \delta_L)}{\sum_{L'=-D}^{D} C(L+L'; \delta_L)},$$

wherein $2D+1 < \Delta_L$ and $$C(L, \delta_L) = \frac{\sum_{L'=-(\Delta_L-1)/2}^{(\Delta_L-1)/2} \sum_{r=r_1}^{r_2} (F(r, L+L') - \overline{F}(L)) \cdot (F(r, L+\delta_L+L') - \overline{F}(L+\delta_L))}{\sqrt{\sum_{L'=-(\Delta_L-1)/2}^{(\Delta_L-1)/2} \sum_{r=r_1}^{r_2} (F(r, L+L') - \overline{F}(L))^2} \cdot \sqrt{\sum_{L'=-(\Delta_L-1)/2}^{(\Delta_L-1)/2} \sum_{r=r_1}^{r_2} (F(r, L+\delta_L+L') - \overline{F}(L+\delta_L))^2}}$$

wherein $\overline{F}(L) = \frac{1}{\Delta_L \cdot (r_2 - r_1)} \cdot \sum_{L'=-(\Delta_L-1)/2}^{(\Delta_L-1)/2} \sum_{r=r_1}^{r_2} (F(r, L+L'))$.

* * * * *